United States Patent
Dreyfuss et al.

(10) Patent No.: US 7,326,222 B2
(45) Date of Patent: Feb. 5, 2008

(54) SUTURE TENSIONING DEVICE

(75) Inventors: Peter J. Dreyfuss, Naples, FL (US); Reinhold Schmieding, Naples, FL (US); Anthony A. Romeo, Burr Ridge, IL (US)

(73) Assignee: Arthrex, Inc., Naples, FL (US)

( * ) Notice: Subject to any disclaimer, the term of this patent is extended or adjusted under 35 U.S.C. 154(b) by 523 days.

(21) Appl. No.: 10/426,882

(22) Filed: May 1, 2003

(65) Prior Publication Data

US 2003/0208210 A1    Nov. 6, 2003

Related U.S. Application Data

(60) Provisional application No. 60/376,544, filed on May 1, 2002.

(51) Int. Cl.
*A61B 17/04* (2006.01)
(52) U.S. Cl. ...................... 606/144; 606/103
(58) Field of Classification Search ............ 623/13.13; 606/60, 53, 88, 74, 72, 144, 148, 232, 103; 140/93.6, 105, 106, 123.5, 123.6
See application file for complete search history.

(56) References Cited

U.S. PATENT DOCUMENTS

| 3,507,270 | A | * | 4/1970 | Ferrier | 600/481 |
|---|---|---|---|---|---|
| 4,712,542 | A | * | 12/1987 | Daniel et al. | 606/96 |
| 5,071,420 | A | * | 12/1991 | Paulos et al. | 606/99 |
| 5,454,821 | A | * | 10/1995 | Harm et al. | 606/148 |
| 5,713,897 | A | * | 2/1998 | Goble et al. | 606/53 |
| 5,788,697 | A | * | 8/1998 | Kilpela et al. | 606/74 |
| 5,797,929 | A | * | 8/1998 | Andreas et al. | 606/148 |
| 5,810,832 | A | * | 9/1998 | Blasingame et al. | 606/103 |
| 5,980,473 | A | | 11/1999 | Korakianitis et al. | |
| 6,547,778 | B1 | | 4/2003 | Sklar et al. | |
| 6,679,889 | B1 | * | 1/2004 | West et al. | 606/88 |
| 6,695,852 | B2 | * | 2/2004 | Gleason | 606/103 |
| 6,723,125 | B2 | * | 4/2004 | Heckele et al. | 623/13.13 |
| 6,761,722 | B2 | * | 7/2004 | Cole et al. | 606/74 |
| 2002/0013608 | A1 | * | 1/2002 | ElAttrache et al. | 606/232 |

\* cited by examiner

*Primary Examiner*—Anhtuan T. Nguyen
*Assistant Examiner*—Tuan V. Nguyen
(74) *Attorney, Agent, or Firm*—Dickstein Shapiro LLP

(57) ABSTRACT

A device for tensioning suture which includes two telescopically slidable cannulated tubes. An adjustment wheel is coupled to and turns a threaded post which is threadingly engaged with the proximal end of one of the slidable tubes. A suture end is passed through the cannulated tubes of the suture tensioning device and secured to the adjustment wheel. Rotating the adjustment wheel counterclockwise increases the overall length of the suture tensioning device and increases tension on the suture.

6 Claims, 4 Drawing Sheets

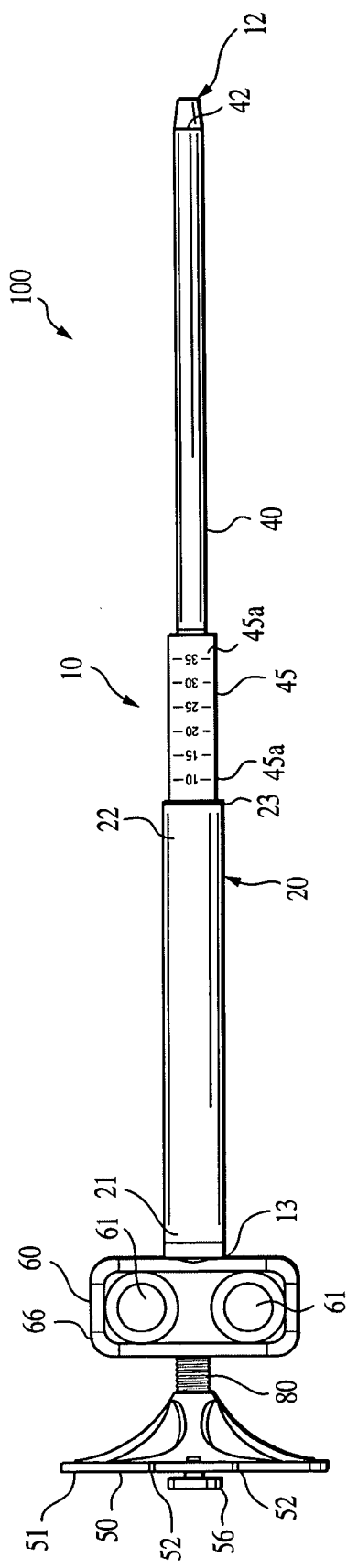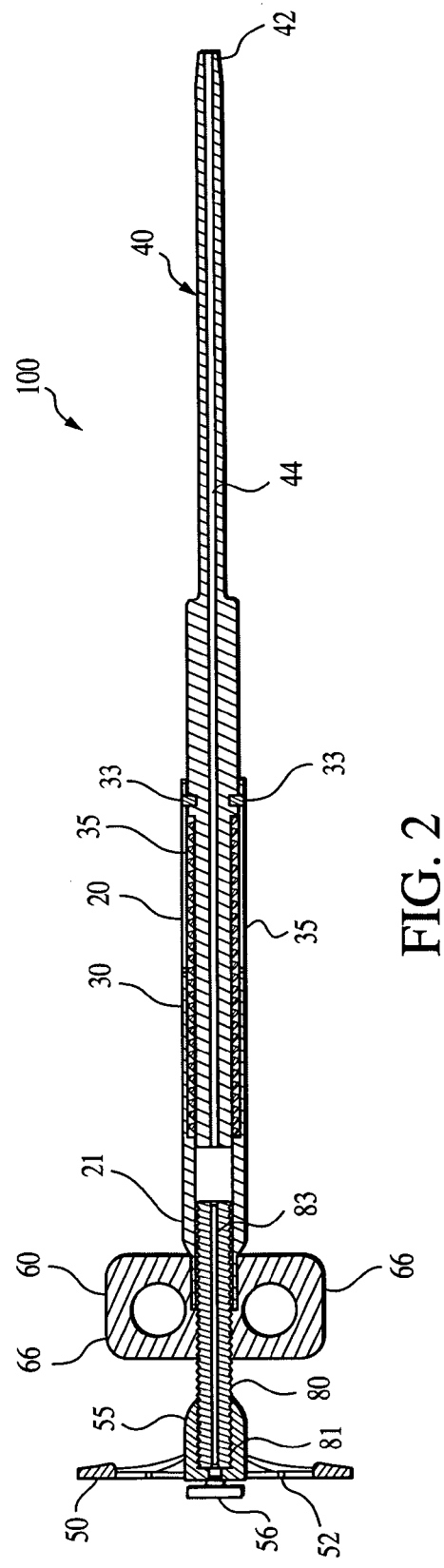
FIG. 1
FIG. 2

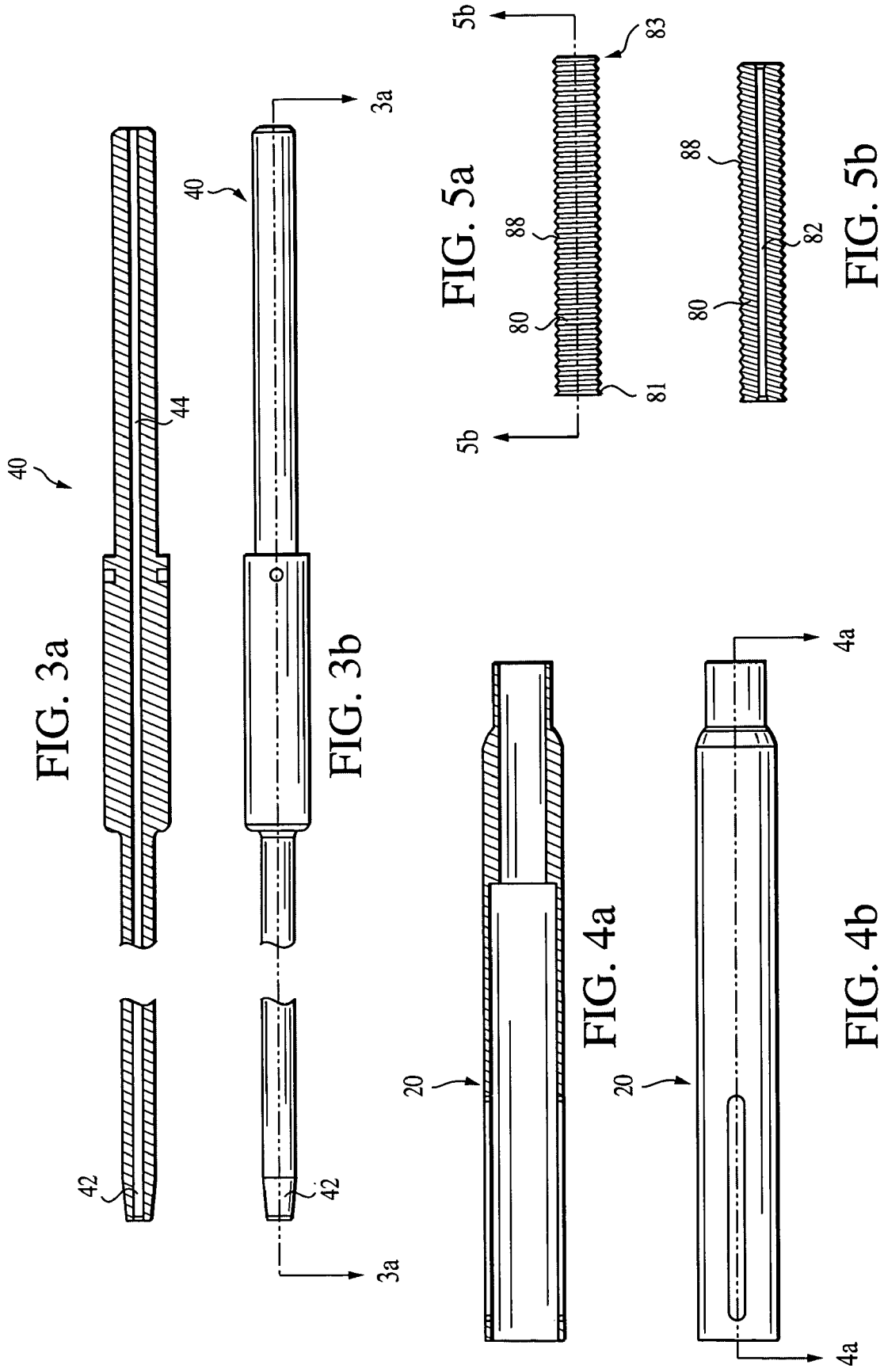

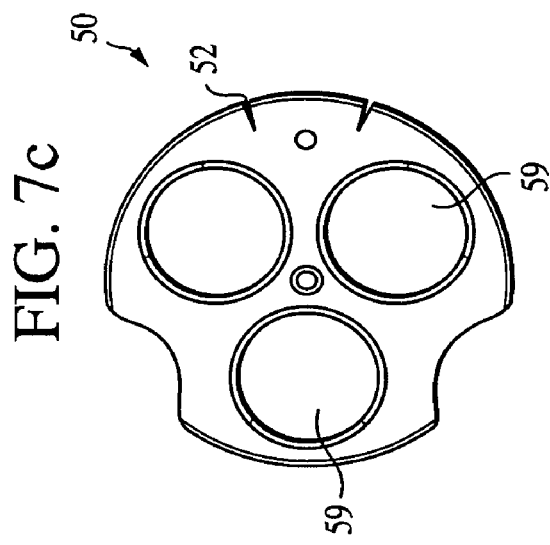
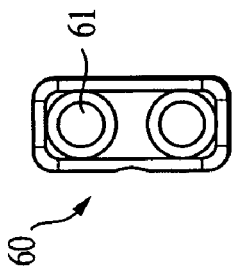
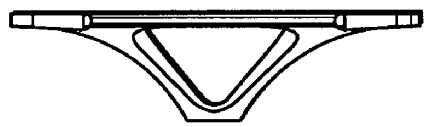
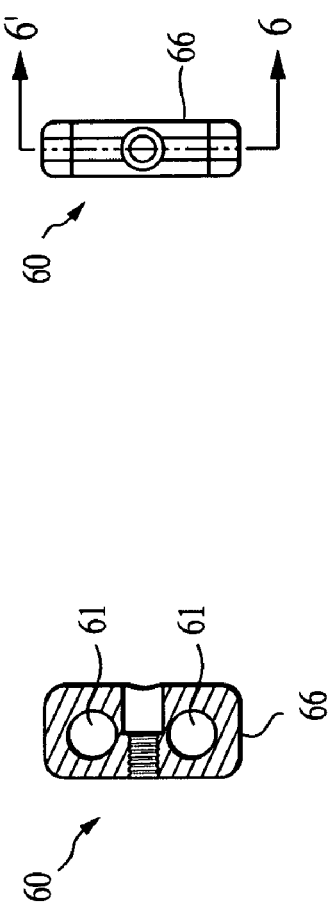
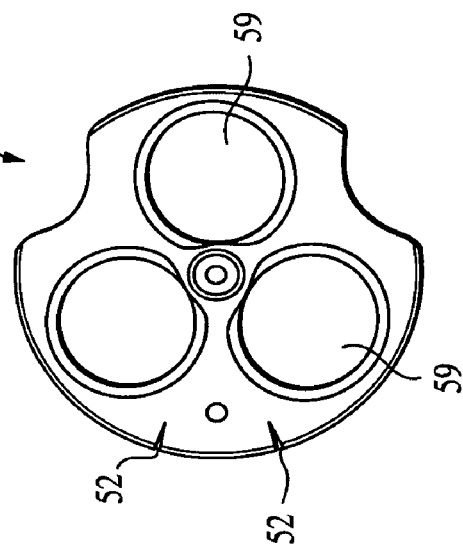

US 7,326,222 B2

SUTURE TENSIONING DEVICE

This application claims the benefit of U.S. Provisional Application Ser. No. 60/376,544, filed May 1, 2002, the entire disclosure of which is incorporated by reference herein.

FIELD OF THE INVENTION

The present invention relates to methods and instruments for tensioning of sutures and, more specifically, to an adjustable suture tensioning device.

BACKGROUND OF THE INVENTION

Bone fixation using cerclage wire is a surgical procedure for securing fractured or weakened bone. Procedures in which bone cerclage may be indicated include, for example, humeral stem fracture repair and total shoulder surgery. After the cerclage wires are tensioned and wrapped, excess wire is cut off. The wire ends are tucked down to be out of the way. Wire ends that are tucked down improperly, or that become loose, can cause irritation and damage and may require additional revision.

An improved surgical technique for encircling a bone with a high strength suture material is needed. Instruments and methods for repairing a bone fracture or for attaching two sections of tissues where placement of a suture, wire or cable is conducted without the tissue damage and irritation presented using cerclage wires are also needed.

SUMMARY OF THE INVENTION

The instruments and methods of the present invention provide an apparatus and methods for cerclage fixation of fractured or weakened bone using high strength suture material. Accordingly, the suture ends can be secured with knots, thereby avoiding the potential for tissue damage and irritation presented using cerclage wires.

In one aspect, the present invention provides a suture tensioning device used for applying tension to a length of high strength suture. The suture tensioning device includes two telescopically slidable cannulated tubes between which a biasing spring is disposed. An adjustment wheel is rotated to turn a threaded post on the end of one of the slidable tubes. A length of suture passes through the cannulated tubes and is secured to the adjustment wheel. Turning the adjustment wheel counterclockwise draws against the suture and compresses the spring, increasing therefore the tension on the suture.

In another embodiment, the invention provides a method of cerclage bone fixation including wrapping the fractured bone with a length of high strength suture material and forming a slip knot in the length of suture. A post leg of the length of suture is threaded through the two cannulated tubes of the suture tensioning device and looped around a post provided on an adjustment wheel. The end of the suture can be secured in a cleat formed on the adjustment wheel. Turning the wheel counterclockwise pulls the suture taut and exerts tension on the suture. A scale provided on the suture tensioning device indicates the relative amount of tension being applied. The tension to be applied by the surgeon on the suture depends on the bone quality and other factors. The tension to be applied generally is greater than that which could be exerted manually, and is typically in the range of 20 lbs.

Other features and advantages of the invention will become apparent from the following description of the invention, which refers to the accompanying drawings.

BRIEF DESCRIPTION OF THE DRAWINGS

FIG. 1 illustrates a perspective view of a suture tensioning device of the present invention.

FIG. 2 illustrates a schematic cross-sectional view of the suture tensioning device of FIG. 1.

FIG. 3(a) illustrates a schematic cross-sectional view of the inner shaft of the suture tensioning device of FIG. 1.

FIG. 3(b) illustrates a perspective view of the inner shaft of the suture tensioning device of FIG. 1.

FIG. 4(a) illustrates a schematic cross-sectional view of the outer shaft of the suture tensioning device of FIG. 1.

FIG. 4(b) illustrates a perspective view of the outer shaft of the suture tensioning device of FIG. 1.

FIG. 5(a) illustrates a perspective view of the post of the suture tensioning device of FIG. 1.

FIG. 5(b) illustrates a schematic cross-sectional view of the post of the suture tensioning device of FIG. 1.

FIG. 6(a) illustrates a schematic cross-sectional view of the thumb pad of the suture tensioning device of FIG. 1.

FIG. 6(b) illustrates a top view of the thumb pad of the suture tensioning device of FIG. 1.

FIG. 6(c) illustrates a schematic cross-sectional view taken along line 6-6' of the thumb pad of FIG. 6(b).

FIG. 7(a) illustrates a top view of the adjustment wheel of the suture tensioning device of FIG. 1.

FIG. 7(b) illustrates a side view of the adjustment wheel of the suture tensioning device of FIG. 1.

FIG. 7(c) illustrates a top view of the adjustment wheel of the suture tensioning device of FIG. 7(a) rotated 180 degrees.

DETAILED DESCRIPTION OF THE PREFERRED EMBODIMENT

Figure 8:
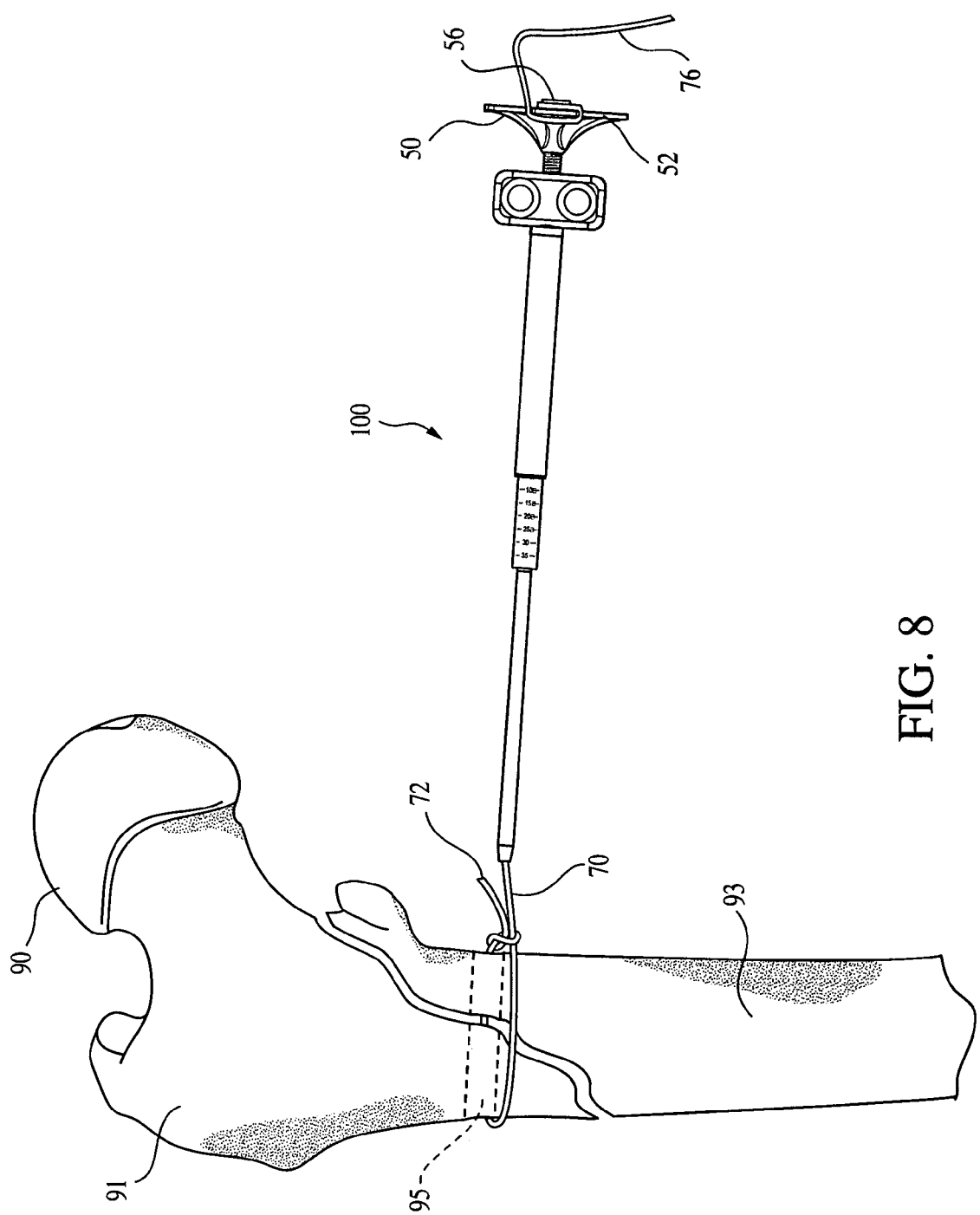
FIG. 8 is a schematic view of a surgical site undergoing a suture tensioning technique according to a method of the present invention.

Referring now to the drawings, where like elements are designated by like reference numerals, FIGS. 1 and 2 illustrate a suture tensioning device 100 of the present invention, while FIGS. 3-7 illustrate various subcomponents of the suture tensioning device 100. Tensioning device 100 includes a cannulated elongated body 10 having a distal end 12 and a proximal end 13, as shown in FIG. 1. The body 10 of the suture tensioning device 100 includes two telescopically slidable sections: an outer shaft or outer tube section 20 and an inner shaft or inner tube section 40. The outer shaft 20 is cannulated for receiving the inner shaft 40. The outer shaft 20 is provided with a proximal end 21 and a distal end 22. A line 23 (FIG. 1) is marked at the distal end 22 of the outer shaft 20 to facilitate reading against scale numbers 45a.

As illustrated in FIGS. 2, 3(a) and 3(b), the inner shaft 40 is also caunnulated and extends to a tapered end 42. In this manner, cannula 44 (FIGS. 2, 3a) of the inner shaft 40 is dimensioned and designed to allow a suture strand to freely pass through the inner and outer tube sections 40, 20, as described below. A cannulated section 45 of inner shaft 40 is provided with scale markings 45a, for indicating tension pressure as described in more detail below. As shown in FIG.

1, cannulated section 45 has a diameter greater than that of the inner shaft 40 but smaller than the diameter of the outer shaft 20.

The outer tube section 20 of FIGS. 2, 4(a) and 4(b) is provided at its proximal end with a thumb pad 60 which is cannulated and is used to prevent the outer shaft 20 from rotating as the suture tensioning device 100 is rotated, as described in more detail below. As shown in more detail in FIG. 6(b), thumb pad 60 has a body 66 with a rectangular configuration and with finger loops 61; however, the invention contemplates other shapes and geometries.

Referring now to FIGS. 1, 2 and 7(a)-(c), the outer tube section 20 is also provided with an adjustment wheel 50 provided with at least one cleat 52. As shown in FIGS. 1 and 2, the adjustment wheel 50 is provided with a suture post 56 disposed on a most distal surface 51 (FIG. 1) of the adjustment wheel 50. The suture post 56 allows a suture strand to wrap around the suture post 56 and be secured in cleat 52. Adjustment wheel 50 is also provided with a plurality of finger loops 59 (FIGS. 7(a), 7(c)) that allow a user to easily maneuver and turn the wheel during the suture tensioning procedure described below.

Adjustment wheel 50 is attached to, and threaded into, the outer tube section 20 by a threaded post 80. A more detailed illustration of the post 80 is shown in FIGS. 5(a)-(b). As illustrated in FIG. 2, proximal end 81 of the post 80 threadingly engages section 55 of the adjustment wheel 50, while distal end 83 of the post 80 threadingly engages distal end 21 of the outer tube section 20. As detailed in FIGS. 5(a)-(b), the post 80 is fully threaded and is provided with a continuous thread 88. Post 80 is also provided with cannulation 82 (FIG. 5b) to allow a suture strand to freely pass through it.

A spring 30 (FIG. 2) is disposed between the inner tube 40 and the inner surface 35 of outer tube 20 and biases the tubes away from each other. As also shown in FIG. 2, a collar is provided within outer tube section 20 to keep the tube sections 20 and 40 aligned and to prevent separation of the tube sections 20, 40.

A method of suture tensioning technique employed in a bone fracture repair, for example, is now described with reference to FIG. 8 and according to an embodiment of the present invention. The present invention may be used to secure, however, any type of tissue, for example bone, cartilage, ligament, graft or tendon, such as a biceps tendon or a rotator cuff, which require suture attachment and appropriate tension.

FIG. 8 illustrates two bone segments 91, 93 of fractured tibia 90 undergoing a stem fracture repair and suture tensioning procedure according to the present invention. A fixation device 95 may be inserted within pre-formed holes within the bone segments 91, 93, or may be directly inserted into the bone segments 91, 93 without previous formation of a hole. As known in the art, the fixation device 95 may be a bone screw or plug, for example, employed with or without a bone plate.

According to a preferred method of fixation of the present invention, a length of high strength suture 70 is employed in connection with the fixation device 95 and is wrapped to secure fractured bone pieces 91, 93. Two half hitches form a slip knot 72, and a post leg 76 of suture 70 is threaded through the tensioning device 100 and secured to post 56 and cleats 52 on the adjustment wheel 50.

For the purposes of the present invention, the term "high strength suture" is defined as any elongated flexible member, the choice of material and size being dependent upon the particular application. For the purposes of illustration and without limitation, the term "suture" as used herein may be a cable, filament, thread, wire, or any other flexible member suitable for tissue fixation in the body. In a preferred embodiment of the invention, the suture comprises a high strength suture sold by the assignee of the present application under the tradename FiberWire.

After threading the high strength suture 70 through the cannulated suture tensioning device 100, the user grasps the thumb pad 60 with one hand, for example the left hand, and turns the adjustment wheel 50 counterclockwise, with the other hand, for example the right hand, to exert tension on the high strength suture 70. Wheel 50 turns, in turn, the threaded post 80 and increases the effective length of outer tube 20. As the length of outer tube 20 increases, tension is absorbed by retaining spring 30, and outer tube 20 moves toward tapered end 42 of inner tube section 40. The relative amount of tension is indicated by the position of line 22 along number scale 45. The amount of tension applied is determined at least in part by the quality of bone involved. The tension to be applied generally is greater than that which could be exerted manually, and is typically in the range of 20 lbs.

Once the desired level of tension has been obtained, slip knot 72 is locked in place as desired by the surgeon, using additional knots, for example. In this manner, the suture is precisely tensioned and positioned at an appropriate distance from the bone sections 91, 93.

Although the above embodiments have been described with reference to a suture tensioning device comprising a biasing spring between two telescopically slidable sections and a scale provided with scale markings for facilitating reading of the exerted tension in the suture, it should be understood that the invention is not limited to these embodiments. Accordingly, the present invention also contemplates a suture tensioning device without a biasing spring between two telescopically slidable sections and without a scale provided with scale markings, as long as the two telescopically slidable sections allow the captured suture to freely slide within the sections and to be properly tensioned by the adjustment wheel.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A suture tensioning device, comprising:
   a first cannulated tube having a proximal end, a distal end and an inner surface;
   a second cannulated tube telescopically slidable within the first cannulated tube so that the second cannulated tube non-rotatably telescopes relative to the first cannulated tube, the second cannulated tube having an outer tubular surface;
   a spring compressibly disposed between the first cannulated tube and the second cannulated tube for biasing the tubes apart, the spring extending between the inner surface of the first cannulated tube and the outer tubular surface of the second cannulated tube;
   a screw having a proximal end and a distal end, the distal end of the screw being threadingly engaged with the proximal end of the first cannulated tube, the proximal end of the screw being engaged with an adjustment device adapted to be coupled to an end of a strand of suture passing through the first and second cannulated tubes, such that rotation of the screw adjusts overall length of the device, thereby adjusting suture tension; and a thumb pad disposed between the most proximal end of the first cannulated tube and the adjustment device, for preventing movement of the first cannulated tube as the screw is rotated.

2. The suture tensioning device of claim 1, wherein the adjustment device is a wheel.

3. The suture tensioning device of claim 1, further comprising a scale provided at the distal end of the second cannulated tube for indicating the suture tension as strand of suture threaded through the first cannulated tube.

4. The suture tensioning device of claim 1, wherein the suture comprises a bioabsorbable material.

5. The suture tensioning device of claim 1, wherein the suture comprises wire.

6. A suture tensioning device, comprising:

a first cannulated tube having a proximal end, a distal end, and an inner surface;

a second cannulated tube telescopically slidable within the first cannulated tube so that the second cannulated tube non-rotatably telescopes relative to the first cannulated tube, the second cannulated tube having an outer tubular surface;

a spring compressibly disposed between the first cannulated tube and the second cannulated tube for biasing the tubes apart, the spring extending between the inner surface of the first cannulated tube and the outer tubular surface of the second cannulated tube;

a screw having a proximal end and a distal end, the distal end of the screw being threadingly engaged with the proximal end of the first cannulated tube, the proximal end of the screw being engaged with an adjustment wheel having a suture post and a plurality of cleats for securing an end of a strand of suture passing through the first and second cannulated tubes, such that rotation of the screw adjusts overall length of the device, thereby adjusting suture tension; and a thumb pad coupled to the first cannulated tube for preventing rotation of the first cannulated tube as the adjustment wheel is rotated.

* * * * *